United States Statutory Invention Registration [19]

[11] Reg. Number: H672

Baxter et al. [43] Published: Sep. 5, 1989

[54] STABLE ANTIFUNGAL CAPSULE FORMULATION

[75] Inventors: Thomas H. Baxter, Skillman; Umesh G. Dalvi, East Brunswick, both of N.J.

[73] Assignee: E. R. Squibb & Sons, Inc., Princeton, N.J.

[21] Appl. No.: 948,379

[22] Filed: Dec. 31, 1986

[51] Int. Cl.[4] ..... A61K 13/00

[52] U.S. Cl. ..... 424/433; 424/404; 424/451; 424/453; 424/456; 264/4.1

[58] Field of Search ..... 424/456, 463, 452, 455

[56] References Cited

U.S. PATENT DOCUMENTS

| | | | |
|---|---|---|---|
| 3,421,282 | 1/1969 | Hasegawa et al. | 424/452 |
| 4,053,489 | 10/1977 | Wirth | 514/864 |
| 4,250,169 | 2/1981 | Hosoi et al. . | |
| 4,291,062 | 9/1981 | Leigh et al. . | |
| 4,404,216 | 9/1983 | Richardson | 514/383 |
| 4,419,352 | 12/1983 | Cox et al. | 514/291 |
| 4,542,020 | 9/1985 | Jackson et al. . | |
| 4,551,148 | 11/1985 | Riley, Jr. et al. . | |

*Primary Examiner*—John F. Terapane
*Assistant Examiner*—Daniel Metzmaier
*Attorney, Agent, or Firm*—Theodore R. Furman, Jr.

[57] ABSTRACT

In accordance with the present invention an antifungal capsule formulation providing enhanced stability for antifungal agents subject to oxidative degradation, e.g. nystatin, is disclosed. The new formulation comprises an antifungal agent, in an amount of from about 0.1 to about 50 percent by weight of the total formulation; and a nonaqueous carrier, throughout which said agent is uniformly dispersed.

Additionally, an antifungal capsule formulation is disclosed wherein thixotropic properties are imparted to the drug carrier system by addition of a gelling agent, such as silicon dioxide. Such thixotropic properties are desired to promote and prolong adhesion of the drug system to the vaginal mucosa in the treatment of vaginal fungal invections.

A low temperature method for fabricating capsules employing such a formulation is also disclosed, said method comprising forming a slurry of the antifungal agent and a nonaqueous liquid carrier, adding a gelling agent, if desired, to the so-formed slurry sufficient to form a thixotropic gel, and encapsulating said gel.

24 Claims, No Drawings

---

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

STABLE ANTIFUNGAL CAPSULE FORMULATION

FIELD OF THE INVENTION

The present invention pertains to an antifungal dosage form providing enhanced stability for sensitive antifungal agents, and more particularly concerns a capsule formulation, preferably containing nystatin, and methods for its use and manufacture.

BACKGROUND OF THE INVENTION

Antifungal agents may be administered in a variety of dosage forms such as creams or ointment, tablets, capsules and suppositories. For example, tablets, suppositories and capsules containing one or more antifungal agents are widely used intravaginally for.the treatment of vaginal candidiasis. Retention of the tablet, capsule or suppository in the vagina and stability of the medicinal agent, during and after manufacture, are of primary importance in the success of such treatment.

Nystatin, for example, has a high degree of sensitivity to heat, oxygen, moisture and extremes in pH. This is due to the highly unsaturated nature of the nystatin molecule. Inactivation of amorphous nystatin occurs even at room temperature and below when subjected to an oxygen source. Elevated moisture conditions and elevated temperatures compound the degradation process. Further, it is believed that once oxidation begins it cannot be stopped, even by storage at −20° C.

Solid nystatin intravaginal tablets typically comprise the medicament, solid binders and about 6 percent by weight of water. The water content, as well as elevated temperatures used during the fabrication of such tablets, can significantly reduce the activity of the drug. Further, premature expulsion of the hard tablet from the vaginal tract can occur.

Jackson et al. U.S. Pat. No. 4,542,020 discloses long-lasting adhesive antifungal suppositories comprising an antifungal agent, e.g. nystatin, together with a hydrocolloid and a low melting suppository base. These suppositories melt at body temperature, releasing the drug-containing hydrooolloid which adheres to the vaginal membrane to provide a uniform distribution of the drug at the site of.the infection. However, the water soluble or hydratable nature of the hydrocolloid can adversely affect the drug's shelf life by allowing and/or contributing to oxidative degradation.

Riley Jr., et al. U.S. Pat. No. 4,551,148, discloses a sustained release vaginal delivery system providing a more uniform release of the medicament over an extended period. In this system, a non-lipoidal internal phase containing the antifungal agent is suspended within the lipoidal external phase. The internal phase actually comprises small drug-containing packets which are diffused throughout the external phase. The external phase in turn provides adhesion to the vaginal membrane at the site of infection. The internal phase disclosed for nystatin, however, contains 60 percent by weight of water, which again can significantly degrade the activity of the nystatin over time.

Leigh et al. U.S. Pat. No. 4,291,062, discloses pharmaceutical compositions for the skin, containing urea, designed to provide good stability and a smooth texture. These compositions comprise a medicament, e.g. nystatin, presented as small particles coated with a wax; an inclusion compound of urea with a straight-chain aliphatic compound; an inert soluble powder; and an inert carrier into which the aforementioned components are suspended. During the formation of these skin treatment compositions, however, the medicament is subjected to a complex process which includes exposure to temperatures of 60° C. and above during the wax-coating procedure.

An antifungal capsule formulation, for use in oral or vaginal capsules, providing enhanced stability for moisture or oxygen sensitive antifungal agents and, in the case of the vaginal capsule formulation, good adhesion to the vaginal membrane. A method for fabricating such capsules would be useful additions to the art.

SUMMARY OF THE INVENTION

In accordance with the present invention a capsule formulation providing enhanced stability for antifungal or antibacterial agents subject to oxidative and hydrolytic degradation, e.g. nystatin, is disclosed. The new formulation comprises, for example, an antifungal agent, in an amount of from about 0.1 to about 50 percent by weight of the total formulation; and a nonaqueous carrier, throughout which said agent is uniformly dispersed.

A method for fabricating capsules avoiding high temperature exposure is also disclosed, said method comprising forming a slurry of the antifungal agent in a nonaqueous liquid and encapsulating said slurry. This process is carried out at or below human body temperature and in a substantially dry and controlled room temperature environment. Optionally, a gelling agent can be added to the so-formed slurry where thixotropic properties are required, as in the case of the vaginal capsule.

DETAILED DESCRIPTION OF THE INVENTION

The improved antifungal capsule formulation of the present invention provides enhanced stability for an antifungal agent by protecting the drug from oxygen and moisture. Thus, a drug such as nystatin, which is highly sensitive to heat, oxygen and moisture, has a substantially greater shelf life, and thereby greater efficacy after months of storage, when fabricated into the formulation of the present invention. In fact, while nystatin in solid vaginal tablets exhibits potency drops of 10–15 percent at room temperature in 3 months and 20–30 percent at 40° C., nystatin stabilized by the present formulation maintains about 98–99 percent of its potency after 3 months storage at 40° C. and no significant loss following storage at ambient room temperature for periods up to 9 months.

The formulation of the present invention, suitable for oral and intravaginal dosage forms, employs a nonaqueous carrier which may be in the form of a liquid or a thixotropic gel. While thixotropic properties are desirable for the vaginally inserted dosage forms, thixotropy is optional for the orally ingested dosage form. A typical thixotropic gel carrier is one that sets in the form of a gel (20,000 to 40,000 centipoise viscosity) but will liquify at room temperature upon application of shear (1000 to 5000 centipoise viscosity). The nonaqueous carrier may comprise a nonaqueous liquid surfactant, such as a sorbitan mono-9-octadecenoate poly(oxy-1,2-ethanediyl) derivative (e.g. TWEEN 80; Atlas Company); an oleaginous liquid, such as mineral oil or a vegetable oil; or, a hydrogenated fat (e.g. Gelucire; Gattefosse Co.) or a mixture of any two or more of these nonaqueous materials. When a thixotropic gel carrier is required, the hydrogenated fat may be employed or a gelling agent such as silicon dioxide or fumigated silicon dioxide (e.g. Aerosil 200; Degussa Company) can be added to one of the nonaqueous liquids. The preferred nonaqueous carrier for an oral capsule in accordance with the present invention is mineral oil and the preferred carrier for the vaginal capsule is a thixotropic gel comprised of mineral oil and fumigated silicon dioxide.

These nonaqueous carriers have been found extremely effective in protecting the antifungal or antibacterial agents from the deleterious effects of oxygen and moisture and thereby seem to render the drugs less susceptible to degradation from the elevated temperatures as well. At the same time, the thixotropic properties of the gel carrier employed in the vaginal capsule provide adhesion of the formulation to vaginal mucosa.

The nonaqueous carrier, exclusive of the antifungal agent, typically comprises from about 90 to about 100 percent by weight and preferably from about 96 to about 100 percent by weight of the nonaqueous liquid surfactant.

The gelling agent, when used, is typically present in the carrier, exclusive of the antifungal agent, in an amount of from about 0 to about 10 percent by weight of the total carrier and preferably in an amount of from about 1 to about 2 percent by weight.

Alternatively, the nonaqueous carrier may comprise from about 90 to about 100 percent by weight of a hydrogenated fat.

The capsule formulation of the present invention will also include one or more antifungal agents, preferably nystatin, dispersed throughout the carrier system in sufficient quantities to maintain an effective concentration for sufficient periods of time so as to produce adequate kill of, for example, *C. albicans*. Thus, the capsule formulation will provide from about 25,000 to about 1,000,000 and preferably from about 75,000 to about 500,000 USP Nystatin units which may be administered up to two times a day or any convenient regimen, such as one capsule 1 or 2 times a day.

Other antifungal agents which may be incorporated into the present formulation include but not limited to amphotericin B, miconazole, ketoconazole, econazole or griseofulvin and antibiotics such as penicillins, cephalosporins, etc. which are degraded by oxidative and/or hydrolytic routes.

An antifungal capsule in accordance with the present invention comprises the above-described capsule formulation encapsulated in any suitable gelatin shell. The antifungal capsule can be administered orally or intravaginally and a water-soluble, soft gelatin shell is preferred for intravaginal administration.

A preferred vaginal antifungal capsule in accordance with the present invention will comprise from about 2 to 4 percent by weight of the formulation of nystatin, from about 94 to about 97 percent by weight of the formulation of mineral oil, from about 1 to about 2 percent by weight of the formulation of silicon dioxide and be encapsulated in a soft, water-soluble, gelatin shell.

A preferred oral capsule formulation in accordance with the present invention will comprise from about 15 to 20 percent by weight of nystatin, from about 73 to 84 percent by weight of mineral oil, and from about 1 to 2 percent by weight of silicon dioxide.

To treat vaginal fungal infections, e.g. vaginal candidiasis, in accordance with the present invention, the above-described antifungal capsule is inserted into the vaginal cavity of a human female. Upon dissolution of the shell the drug-containing thixotropic gel is released and adheres to the vaginal mucous membrane by reason of its thixotropy providing release of the drug in that area.

Also, in accordance with the present invention is the low temperature method for fabrication of the antifungal capsules. This method drastically improves the product in that it avoids exposure of the drug to temperatures above human body temperature thereby substantially minimizing oxidative and hydrolytic degradation.

To carry out present methods a suitable amount of the desired antifungal agent, or agents, is added to and mixed with a nonaqueous liquid carrier so that a slurry is formed. Thereafter, the gelling agent, when used, is added to the slurry so that a carrier/drug thixotropic gel forms upon setting. The so-formed system is finally encapsulated, preferably in a water-soluble, soft gelatin shell. The method should be carried out in a low humidity, controlled room temperature environment. To fabricate formulations using hydrogenated fat carriers, the fat should be heated to about human body temperature prior to addition of the drug therein.

The following working examples represent specific embodiments of the present invention, however, the scope of the present invention is not meant to be limited by the details described therein. In all of the examples, the percentage values in the stability tables are expressed as a percentage of the initial potency.

EXAMPLE 1

An antifungal capsule formulation in accordance with the present invention having the following composition was prepared as described below.

| Ingredient | Amount (g) |
|---|---|
| Nystatin* (100,000 USP units) | 160 |
| Mineral Oil, USP | 7,720 |
| Fumigated Silicon dioxide (Aerosil 200) | 120 |
| TOTAL | 8,000 g |

*Actual weight dependent on assay

To 7,720 grams of mineral oil (USP) was added 160 grams of nystatin powder having a particle size of about 1 to 50 microns. At room temperature (~20° C.) the drug was thoroughly dispersed in the oil to form a slurry using a standard homogenizer. Slowly, 120 grams of the fumigated silicon dioxide was added to the slurry and uniformly dispersed. The so-formed mixture was stored at controlled room temperature for about 60 minutes to form a thixotropic gel.

Using a Brookfield LVt viscometer with spindle #3, the viscosity of the gel was tested and the results are summarized below.

| Viscosity (measured at 25° C.) | |
|---|---|
| RPM | CPS |
| 0.3 | 112,000 |
| 0.6 | 59,400 |
| 1.5 | 28,560 |
| 3.0 | 16,800 |

The formulation was thereafter sencapsulated in soft, water-soluble, gelatin shells to form 8,000 vaginal capsules, each capsule containing 1000 mg of the formulation.

EXAMPLE 2

An antifungal capsule formulation in accordance with the present invention having the following composition was prepared as described in Example 1.

| Ingredient | Amount (g) |
|---|---|
| Nystatin* (100,000 USP units) | 160 |
| TWEEN 80 (Sorbitan mono-9-octadecenoate poly(oxy-1,2-ethanediyl) derivative) | 7,720 |
| Fumigated Silicon dioxide (Aerosil 200) | 120 |
| TOTAL | 8,000 g |

*Actual weight dependent on assay

The formulation ws stored at controlled room temperature for 60 minutes. The viscosity results using Brookfield LVt viscometer with spindle #3 are summarized below.

| Viscosity (measured at 25° C.) | |
|---|---|
| RPM | CPS |
| 0.3 | 68,000 |
| 0.6 | 36,000 |
| 1.5 | 19,000 |
| 3.0 | 12,400 |

This formulation was thereafter encapsulated in soft water-soluble gelating shells to form 8,0000 vaginal capsules, each capsule containing 1000 mg of the formulation.

EXAMPLE 3

An antifungal capsule formation in accordance with the present invention having the following composition was prepared as described below.

| Ingredient | Amount (g) |
|---|---|
| Nystatin* (100,000 USP units) | 160 |
| Gelucire 35/10 (hydrogenated fat) | 7,840 |
| TOTAL | 8,000 g |

*Actual weight dependent on assay 7,840 grams of gelucire 35/10 was heated to about 35° C. There after 160 grams of nystatin was added and uniformly dispersed using a standard homogenizer. Upon cooling to room temperature (about 3 hours), the so-formed mixture set to a gel. This formulation was thereafter encapsulated in soft, water-soluble, gelatin shells to form 8,000 vaginal capsules, each capsule containing 1000 mg of the formulation.

EXAMPLE 4

An oral nystatin capsule formulation was made as described in Example 1 and having the following composition.

| Ingredient | Amount (g) |
|---|---|
| Nystatin* (500,000 USP units) | 700 |
| Mineral Oil, USP | 2,782.5 |

-continued

| Ingredient | Amount (g) |
|---|---|
| Fumigated Silicon dioxide (Aerosil 200) | 17.5 |
| TOTAL | 3,500 g |

*Actual weight dependent on assay

This formulation was thereafter encapsulated in hard, water-solbule, two piece gelatin shells to form 7,000 oral capsules, each capsule containing 500 mg of the formulation.

EXAMPLE 5

An oral nystatin capsule formulation was made as described in Example 2 and having the following composition.

| Ingredient | Amount (g) |
|---|---|
| Nystatin (500,000 USP units) | 700 |
| TWEEN 80 | 2,782.5 |
| Fumigated Silicon dioxide (Aerosil 200) | 17.5 |
| TOTAL | 3,500 g |

This formulation was thereafter encapsulated in soft, water, water-soluble, gelating shells to form 7,000 oral capsules, each capsule containing 500 mg of the formulation.

EXAMPLE 6

An oral nystatin capsule formulation was made as described in Example 3 and having the following composition.

| Ingredient | Amount (g) |
|---|---|
| Nystatin (500,000 USP units) | 700 |
| Gelucire 35/10 (Hydrogenated fat) | 2,800 |
| TOTAL | 3,500 g |

This formulation was thereafter encapsulated in soft, water-soluble, gelatin shells to form 7,000 capsules, each containing 500 mg of the formalation.

COMPARITIVE EXAMPLE

A batch of solid nystatin vaginal tablets, in accordance with the prior art, having the following composition was manufactured as described below.

| Ingredient | mg/tablet |
|---|---|
| Nystatin* (120,000 USP units) | 24 |
| Ethylcellulose Type N-22 | 20 |
| Corn Starch USP | 33 |
| Stearic Acid NF | 22 |
| Lactose | 1,101 |
| TOTAL | 1,200 g |

*Actual weight dependent on assay

The weighed quantities of the ingredients to make a 5,000 tablet batch were transferred to a blender and thoroughly mixed until uniform and compressed into tablets each weighing about 1200 mg. These tablets were placed in plastic bottles with plastic closures and stored at 20° C. and 40° C. The potency of the nystatin tablets was checked and is expressed below as a percent of the initial potency.

| Prior Art Vaginal Tablet Stability | | |
|---|---|---|
| Initial Potency | 20° C. 120,000 (USP Units) | 40° C. 120,000 (USP Units) |
| 1 month | 91% | 82% |
| 3 months | 88% | 73% |

As a comparison the oral capsules as fabricated in Example 4 using two piece hard gelatin capsules were tested under the same conditions. The results, which show a substantially improved stability for the nystatin over time and a reduced sensitivity to temperature are summarized below.

| Nystatin Capsule (from Ex. 4) | −20° C. | 4° C. | 20° C. | 32° C. | 40 ° C. |
|---|---|---|---|---|---|
| Initial Potency (units) | 504,318 | 504,318 | 504,318 | 504,318 | 504,318 |
| 1 month | 96% | 98% | 99% | 99% | 99% |
| 3 months | — | 98% | 98% | 99% | 99% |
| 6 months | 96% | 96% | 99% | 96% | 96% |
| 9 months | — | 96% | 95% | 97% | 95% |

Also, as a comparison, oral capsules as fabricated 2, 3, 5, and 6 were tested under the same conditions. The results, which show a substantially improved stabililty for the nystatin over time and a reduced sensitivity to temperature are summarized below.

| Nystatin Stability* | | | |
|---|---|---|---|
| | Initial Potency | 1 month | 3 months |
| Example 1 | | | |
| 4° C. | | 92% | 96% |
| RT | 105,000 | 94% | 93% |
| 40° C. | | 94% | 93% |
| Example 2 | | | |
| 4° C. | | 102% | 100% |
| RT | 96,100 | 99% | 101% |
| 40° C. | | 99% | 97% |
| Example 3 | | | |
| 4° C. | | 98% | 99% |
| RT | 99,100 | 102% | 99% |
| 40° C. | | 99% | 98% |
| Example 4 | | | |
| 4° C. | | 102% | 101% |
| RT | 513,000 | 104% | 100% |
| 40° C. | | 103% | 101% |
| Example 5 | | | |
| 4° C. | | 106% | 106% |
| RT | 507,000 | 103% | 107% |
| 40° C. | | 103% | 101% |

*numbers represent USP units of activity

What is claimed is:

1. An antifungal capsule formulation suitable for oral or vaginal use comprising an antifungal or antibacterial agent subject to oxidative or hydrolytic degradation in an amount of from about 0.1 to about 50 percent by weight of the total formulation; and a nonaqueous carrier throughout which said agent is uniformly dispersed, thereby providing stability to said agent.

2. The formulation of claim 1 wherein said nonaqueous carrier is selected from the group consisting of nonaqueous liquid surfactants and hydrogenated fats or mixtures thereof.

3. The formulation of claim 2 wherein said carrier comprises a nonaqueous liquid surfactant selected from the group consisting of sorbitan mono-9-octadecenoate poly(oxy-1,2-ethanediyl) derivatives, oleaginous liquids and mixtures thereof.

4. The formulation of claim 3 wherein said oleaginous liquid is selected from the group consisting of mineral oil, vegetable oils and mixtures thereof.

5. The formulation of claim 3 wherein said nonaqueous carrier includes said nonaqueous liquid surfactant in an amount of from about 90 to about 100 percent by weight of the total carrier.

6. The formulation of claim 2 wherein said nonaqueous carrier includes said nonaqueous liquid surfactant in an amount of from about 96 to about 100 percent by weight of the total carrier.

7. The formulation of claim 1 wherein said nonaqueous carrier is a thixotropic gel.

8. The formulation of claim 7 wherein said carrier further comprises a sufficient amount of gelling agent selected from the group consisting of silicon dioxide or fumigated silicon dioxide to render the carrier thixotropic.

9. The formulation of claim 8 wherein said carrier includes gelling agent in an amount of from about 0.1 to about 10 percent by weight of the total carrier.

10. The formulation of claim 7 wherein said nonaqueous carrier comprises a nonaqueous hydrogenated fat.

11. The formulation of claim 10 wherein the nonaqueous carrier includes said fat in an amount of from about 90 to about 100 percent by weight of the total carrier.

12. The capsule formulation of claim 1 wherein said antifungal or antibacterial agent is selected from the group consisting of nystatin, amphotericin B, miconazole, ketoconazaole, econazole or griseofulvin, penicillins and cephalosporins.

13. The formulation of claim 12 wherein said antifungal agent is nystatin.

14. The formulation of claim 13 containing from about 25,000 to about 1,000,000 USP units of nystatin.

15. The formulation of claim 13 wherein the nystatin has a particle size of from about 1 to about 50 microns.

16. A vaginal antifungal capsule comprising a formulation which includes between about 2 and 4 percent by weight of nystatin, between about 94 and 97 percent by weight of mineral oil and between about 1 and 2 percent by weight of silicon dioxide; said formulation being encapsulated in a soft, water-soluble gelatin shell.

17. An oral antifungal capsule formulation which includes between about 15 and 25 percent by weight of nystatin, between about 73 and 84 percent by weight of mineral oil and between about 1 and 2 percent by weight of silicon dioxide.

18. A method of treating vaginal candidiasis which comprises administering to the human vaginal cavity in need of such treatment the antifungal soft capsule of claim 16, including a therapeutically effective amount of said capsule formulation, such that upon dissolution of the soft gelatin shell, said thixotropic gel carrier will adhere to the vaginal mucous membrane thereby delivering said antifungal agent thereto.

19. A low temperature method of fabricating antifungal capsules with enhanced stability comprising (a) forming a slurry by mixing a suitable amount of an antifungal or antibacterial agent in a nonaqueous liquid carrier;

(b) encapsulating the so-formed, drug-containing slurry in a suitable shell; and (c) carrying out parts (a) and (b) in a substantially dry, room temperature environment.

20. The method of claim 19 wherein a gelling agent is added to the slurry in an amount sufficient to form a thixotropic gel.

21. The method of claim 19 wherein said antifungal or antibacterial agent is selected from the group consisting of nystatin, amphotericin B, miconazole, ketoconazole, econazole or griseofulvin, penicillins or cephalosporins.

22. The method of claim 21 wherein said antifungal agent is nystatin.

23. The method of claim 22 wherein said nonaqueous liquid is selected from the group consisting of sorbitan mono-9-octadecenoate poly(oxy-1,2-ethanediyl) derivatives or oleaginous liquids and wherein said gelling agent is selected from the group consisting of silicon dioxide or fumigated silicon dioxide.

24. The method of claim 23 wherein said oleaginous liquid is selected from the group consisting of mineral oil or a vegetable oil.

* * * * *